US008541225B2

(12) United States Patent
Hazlebeck et al.

(10) Patent No.: US 8,541,225 B2
(45) Date of Patent: Sep. 24, 2013

(54) SYSTEM AND METHOD FOR USING A PULSE FLOW CIRCULATION FOR ALGAE CULTIVATION

(75) Inventors: David A. Hazlebeck, El Cajon, CA (US); Jiping Zhang, San Diego, CA (US); Xiaoxi Wu, Encinitas, CA (US)

(73) Assignee: General Atomics, San Diego, CA (US)

( * ) Notice: Subject to any disclaimer, the term of this patent is extended or adjusted under 35 U.S.C. 154(b) by 0 days.

(21) Appl. No.: 13/189,737

(22) Filed: Jul. 25, 2011

(65) Prior Publication Data
US 2013/0029403 A1  Jan. 31, 2013

(51) Int. Cl.
*C12N 1/12* (2006.01)
*C12M 1/36* (2006.01)

(52) U.S. Cl.
USPC .................................. 435/257.1; 435/286.7

(58) Field of Classification Search
USPC .......................................... 435/257.1, 286.7
See application file for complete search history.

(56) References Cited

U.S. PATENT DOCUMENTS

| | | | |
|---|---|---|---|
| 2,732,663 A | 1/1956 | Dewey, II | |
| 2,854,792 A | 10/1958 | Juda | |
| 2,949,700 A | 8/1960 | Kathrein | |
| 3,195,271 A | 7/1965 | Golueke et al. | |
| 3,218,758 A | 11/1965 | Konikoff | |
| 3,446,488 A | 5/1969 | Mail et al. | |
| 3,468,057 A | 9/1969 | Buisson et al. | |
| 3,521,400 A | 7/1970 | Ort | |
| 3,958,364 A | 5/1976 | Schenck et al. | |
| 4,087,936 A | 5/1978 | Savins et al. | |
| 4,236,349 A | 12/1980 | Ramus | |
| 4,253,271 A | 3/1981 | Raymond | |
| 4,391,887 A | 7/1983 | Baumgarten et al. | |
| 4,417,415 A | 11/1983 | Cysewski et al. | |
| 4,958,460 A | 9/1990 | Nielson et al. | |
| 5,116,506 A | 5/1992 | Williamson et al. | |
| 5,330,913 A | 7/1994 | Nakayama | |
| 5,522,985 A | 6/1996 | Bender et al. | |
| 5,843,762 A | 12/1998 | Moll | |
| 5,951,875 A | 9/1999 | Kanel et al. | |
| 6,000,551 A | 12/1999 | Kanel et al. | |
| 6,335,191 B1 * | 1/2002 | Kiplinger et al. ........... 435/252.1 |
| 6,395,521 B1 | 5/2002 | Miura | |
| 6,524,486 B2 | 2/2003 | Borodyanski et al. | |
| 7,467,023 B2 | 12/2008 | Brown | |
| 7,638,314 B2 | 12/2009 | Zappi et al. | |
| 7,662,616 B2 | 2/2010 | Hazlebeck et al. | |
| 7,687,261 B2 | 3/2010 | Hazlebeck et al. | |
| 7,763,457 B2 | 7/2010 | Dunlop et al. | |
| 7,977,076 B2 | 7/2011 | Oyler | |
| 2005/0112735 A1 | 5/2005 | Zappi et al. | |
| 2006/0051274 A1 | 3/2006 | Wright et al. | |
| 2007/0048848 A1 | 3/2007 | Sears | |
| 2007/0072285 A1 | 3/2007 | Barringer | |
| 2007/0138070 A1 | 6/2007 | Dimitriou et al. | |
| 2008/0009055 A1 | 1/2008 | Lewnard | |
| 2008/0086937 A1 | 4/2008 | Hazlebeck et al. | |
| 2008/0086938 A1 | 4/2008 | Hazlebeck et al. | |
| 2008/0087165 A1 | 4/2008 | Wright et al. | |
| 2008/0133039 A1 | 6/2008 | Brown | |
| 2008/0299643 A1 | 12/2008 | Howard et al. | |
| 2009/0081743 A1 | 3/2009 | Hazlebeck et al. | |
| 2009/0081748 A1 | 3/2009 | Oyler | |
| 2010/0120104 A1 | 5/2010 | Reed | |
| 2010/0260618 A1 * | 10/2010 | Parsheh et al. ............. 417/178 |
| 2010/0327077 A1 * | 12/2010 | Parsheh et al. ............. 239/71 |
| 2011/0023360 A1 * | 2/2011 | Ryan et al. .................. 47/62 C |

FOREIGN PATENT DOCUMENTS

| | | |
|---|---|---|
| WO | 2010002745 A1 | 1/2010 |
| WO | 2010002745 A1 | 7/2010 |
| WO | 2011022349 A1 | 2/2011 |

OTHER PUBLICATIONS

Sheehan, et al., NREL/TP-580-24190 A Look Back at the U.S. Department of Energy's Aquatic Species Program: Biodiesel from Algae, U.S. Department of Energy's Office of Fuels Development, Jul. 1998.
Miao, et al, Biodiesel Production from Heterotrophic Microalgal Oil, Bioresource Technology 97 (2006), pp. 841-846, Department of Biological Sciences and Biotechnology, Tsinghua University, Beijing 10084, PR China.
Spolaore, et al., Commercial Applications of Microalgae, Journal of Bioscience and Bioengineering, vol. 101, No. 2, 87-96, 2006, Laboratoire de Genie des Procedes et Materiaux, Ecole Centrale Paris, Paris, France.
Medina, et al., Downstream Processing of Algal Polyunsaturated Fatty Acids, Biotechnology Advances, vol. 16, No. 3, pp. 517-580, 1998, Elsevier Science Inc., USA.
Barbosa, et al., Optimisation of Cultivation Parameters in Photobioreactors for Microalgae Cultivation Using the A-stat Technique, Biomolecular Engineering 20 (2003), pp. 115-123, Elsevier Science B.V.
S. Heubeck and R. Craggs, "Resource Assessment of Algae Biomass for Potential Bio-Energy Production in New Zealand," New Zealand Forest Research Institute Limited, NIWA Client Report: HAM2007-157, Oct. 2007, NIWA Project: SCI08282, National Institute of Water & Atmospheric Research Ltd., Hamilton, New Zealand.
NIWA (National Institute of Water & Atmospheric Research), "Bio-oil from Wastewater Algae," online article published at www.niwa.co.nz, May 21, 2009.

* cited by examiner

*Primary Examiner* — Karen Cochrane Carlson
*Assistant Examiner* — Natalie Moss
(74) *Attorney, Agent, or Firm* — Nydegger and Associates

(57) ABSTRACT

A system and method for using a pulse flow to circulate algae in an algae cultivation apparatus are provided. In order to counteract the negative effects of biofouling on algae cultivation equipment, a pulse flow is created to periodically move through an algae cultivation apparatus. The pulse flow will dislodge algae cells adhering to various surfaces of the apparatus, and it will also create turbulence to stir up any algae cells which may have settled onto the bottom of the apparatus. To produce an increased fluid flow rate required to create an effective pulse flow, a sump, which is periodically filled with drawn algal culture from the apparatus, is located at an elevated position above the apparatus. When released, the algal culture travels through a transfer pipe and into the apparatus with gravity causing the algal culture to flow at a very high rate.

13 Claims, 2 Drawing Sheets

SYSTEM AND METHOD FOR USING A PULSE FLOW CIRCULATION FOR ALGAE CULTIVATION

FIELD OF THE INVENTION

The present invention pertains generally to systems and methods for growing algae. More particularly, the present invention pertains to the use of a system that can continuously grow algae in a more efficient manner by minimizing complications caused by biofouling. The present invention is particularly, but not exclusively, useful as a system for increasing the productivity of algae growth systems by using a pulse flow to periodically stir and rinse the algae cultivation apparatus.

BACKGROUND OF THE INVENTION

As worldwide petroleum deposits decrease, there is rising concern over petroleum shortages and the costs that are associated with the production of carbon-based fuel sources. As a result, alternatives to products that are currently processed from petroleum are being investigated. In this effort, biofuel has been identified as a possible alternative to petroleum-based fuels. In general, a biodiesel is a fuel comprised of mono-alkyl esters of long chain fatty acids derived from plant oils or animal fats. In industrial practice, biodiesel is created when plant oils or animal fats are reacted with an alcohol, such as methanol.

Apart from using animal fats, the creation of biofuels from plant oils has gained wide attention in recent years. The process of creating biofuel from plant oils, of course, necessarily begins by growing and harvesting plants such as algae cells. In particular, algae is known to be one of the most efficient plants for converting solar energy into cell growth, so it is of particular interest as a biofuel source.

In an algae cultivation system, the algae cells are typically grown in a cultivation apparatus as part of a liquid medium that is exposed to sunlight to promote photosynthetic growth. Further, the algae cell growth process normally requires the liquid medium to be continuously circulated through the system to allow algae cells to ingest nutrients. Three of the most prevalent algae cultivation apparatuses in use today which meet these requirements are: (1) a photobioreactor, (2) a cultivation pond with a circulation device, and (3) a cultivation pond without a circulation device. Despite having numerous advantages when growing algae, these apparatuses have significant disadvantages, many of which involve biofouling. With biofouling, algae cells tend to adhere to or accumulate on various surfaces. In particular, the algae cells adhere to a light transmitting cover and to the bottom and walls of the apparatus. Importantly, biofouling can significantly decrease the productivity of an algae cultivation system. In detail, if biofouling occurs because algae cells adhere to the light transmitting cover, photosynthesis is disrupted as less light reaches algae cells. In addition, when algae cells remain stationary on a surface, several problems arise: (1) algae cells may die and provide a food source for contaminants like protozoa; (2) algae cells settled too deep below the surface of the water will not receive enough light; and (3) algae cells will not move enough to ingest nutrients floating in the algal culture. All of these problems cause significant disruptions to an effective algae cultivation system.

Various efforts have been made to continuously circulate algal culture. Yet, biofouling still causes significant problems to algae cultivation systems. For one, system efficiency is hindered as algae cultivation systems must be drained and cleaned often to remove the algae cells that have adhered to various surfaces. These interruptions can be minimized by using a device or method that forcefully removes algae cells from surfaces and also serves as an impetus to circulate algae cells in the system.

In light of the above, it is an object of the present invention to provide a system and method for growing algae for biofuel production which minimizes the effects of biofouling. Another object of the present invention is to provide a system and method for growing algae that uses a pulse flow to increase the efficiency of the system. Yet another object of the present invention is to provide a system and method for growing algae using pulse flow circulation that is simple to implement, easy to use, and comparatively cost effective.

SUMMARY OF THE INVENTION

In accordance with the present invention, a system and method for using a pulse flow to circulate algae in an algae cultivation system is provided. An essential element of the present invention is the use of an elevated flush tank that is used to create the pulse flow. When it is created, the pulse flow circulates algae cells and dislodges any algae cells clinging to various components of the algae cultivation system.

Structurally, the system of the present invention may be adapted for use with any type of algae cultivation device presently in use, or the system may be used as a stand-alone algae cultivation system. The two most common devices for cultivating algae in use today are a photobioreactor or a pond (with or without a circulation device). The present invention can be adapted for use with either type of device. For comparison purposes, the photobioreactor is a closed system that most often has a vertical configuration, while the pond is an open system and is built in a horizontal configuration onto a surface. In either case, a flush tank is provided to store a fixed amount of algal culture effluent which has been drawn from the algae cultivation device. As contemplated for the present invention, the flush tank is situated higher than the cultivation device and is connected to the cultivation device by a conduit. To account for this difference in elevation, a circulation pump is provided to move the effluent from the cultivation device into the flush tank. This pump is usually located at an access point or a drainage point of the algae cultivation device. To be more specific, because a photobioreactor is usually constructed with a vertical orientation, an access or drainage point is most often situated at the bottom of the photobioreactor. And, a cultivation pond will have a designated drainage or access point for removing liquid from the pond. In either case, a conduit is connected between the circulation pump and the flush tank. In addition, a gas exchange tank may also be included in the system to add carbon dioxide ($CO_2$) to a portion of the drawn effluent while, at the same time, removing oxygen ($O_2$). The gas exchange tank is included in the system to promote algae growth by providing $CO_2$ to be used as a nutrient source by algae cells. As envisioned for the present invention, the gas exchange tank receives algal effluent drawn from the algae cultivation device, enriches the effluent with $CO_2$, and reintroduces the $CO_2$-rich effluent back into the cultivation device through a return pipe. Furthermore, the gas exchange tank and the flush tank can be the same one.

Several components may be provided to govern the release of the effluent from the flush tank. For one, a timer may be connected to the flush tank to release the effluent at a predetermined time. In another embodiment, a level switch is connected to the flush tank to release the effluent once the flush tank reaches a preplanned capacity level. As envisioned for the present invention, the timer and the level switch are both included for use with the system. Alternatively, the flush tank may also be manually activated with an activation switch. With any of the activation methods, a gate valve is moved from a closed position to an open position to release the fluid from the flush tank into a transfer pipe connected to the algae cultivation device. Upon activation, a pulse flows rapidly from the flush tank into the algae cultivation device.

In operation, the system of the present invention begins by drawing a portion of algal culture from the algae cultivation device to create an effluent. The effluent is then pumped, using the circulation pump, into the flush tank via the conduit. The effluent remains in the flush tank until it is released in one of the following ways: (1) the flush valve is manually opened; (2) the timer initiates the activator to open the flush valve; or (3) a level switch initiates the flush valve to release the effluent once the effluent reaches a predetermined level in the flush tank. It should be noted that the system may use any combination of the preceding methods for releasing effluent from the flush tank. Upon release, and due primarily to the elevation difference between the cultivation device and the flush tank, the effluent will flow rapidly out of the flush tank and into the cultivation device through a transfer pipe to create a pulse flow of effluent. Due to the sudden increase in the fluid flow rate, the pulse flow will dislodge any algae cells which are attached to any surface of the cultivation device. Additionally, the pulse flow will cause turbulence in the algae cultivation device. This turbulence will cause most, if not all, of the algae cells, which have settled onto the bottom of the cultivation device, to become suspended once again in the algal culture. This movement of the algae cells will promote photosynthesis and improve access to nutrients floating in the culture. In most cases, the direction of flow for the pulse flow will be the same direction as the flow in the cultivation device. Yet, the system may also reverse the flow direction of the pulse flow to go in the opposite direction of the algal culture flow in the cultivation device.

Once the effluent is released, the flush tank is emptied, and a new pulse flow cycle, or flush cycle, can begin. A new cycle begins when the flush valve is closed and the pump draws effluent to fill the flush tank.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
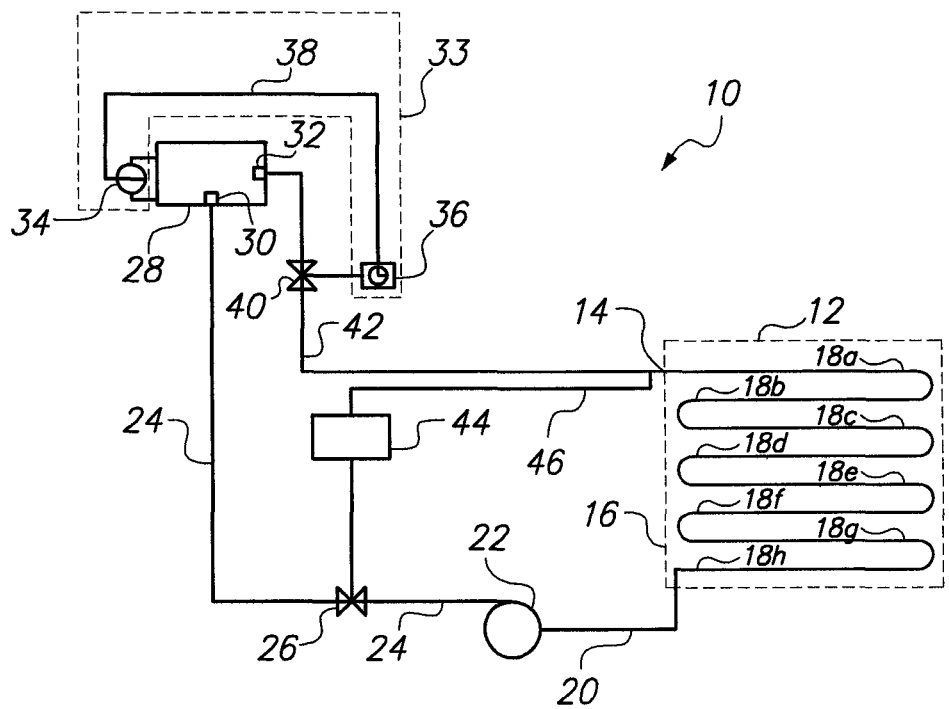
FIG. 1 is a schematic diagram of the layout of the system for the present invention when used in conjunction with a photobioreactor (PBR)

Initially referring to FIG. 1, a system of the present invention is shown and is generally designated 10. In FIG. 1, the system 10 is shown when used in conjunction with a photobioreactor 12 having an inlet 14 for introducing algal culture into the photobioreactor 12 and an outlet 16 for removing algal culture from the photobioreactor 12 as needed. In addition, the photobioreactor 12 is built with a plurality of flow channels 18a-h with algal culture traveling through the photobioreactor starting at flow channel 18a. As shown, the outlet 16 of the photobioreactor 12 is connected to a transfer pipe 20 through which circulation pump 22 can draw a portion of growing algal culture out of the photobioreactor 12. Furthermore, the circulation pump 22 is connected to a conduit 24 which includes a diverting valve 26 that is used to redirect algal culture from the conduit 24. The diverting valve 26 remains in a closed position when algal culture is being pumped to a flush tank 28, which is constructed with an inlet 30 and an outlet 32. As required for the present invention, the flush tank 28 stores drawn algal culture until released. In order to release the drawn algal culture, an activator 33 is provided. In FIG. 1, it can be seen that the activator 33 comprises a level switch 34 or a timer 36 electrically connected by a signal wire 38. Once initiated, the activator 33 will open gate valve 40 to release the drawn algal culture into a transfer pipe 42 connected between the flush tank 28 and the inlet 14 of the photobioreactor 12.

In order to promote algae growth, a gas exchange tank 44 is provided to provide $CO_2$ to algal culture in the photobioreactor 12. To do this, the diverting valve 26 is opened and effluent is pumped out of the photobioreactor 12. This effluent is diverted to the gas exchange tank 44 where $CO_2$ is added to the effluent and $O_2$ is removed. Once this gas exchange process is completed, the effluent from the gas exchange tank 44 will travel through a return pipe 46 to the photobioreactor 12 to provide nutrients to the growing algal culture. As envisioned for the present invention, diverting effluent to the gas exchange tank 44 can be accomplished independent of filling the flush tank 28 or at the same time as the flush tank 28 is filled, or the system can be arranged so that the flush tank is used for gas exchange purposes as well, and therefore the independent gas exchange tank 44 and the diverting valve 26 can be eliminated.

Figure 2:
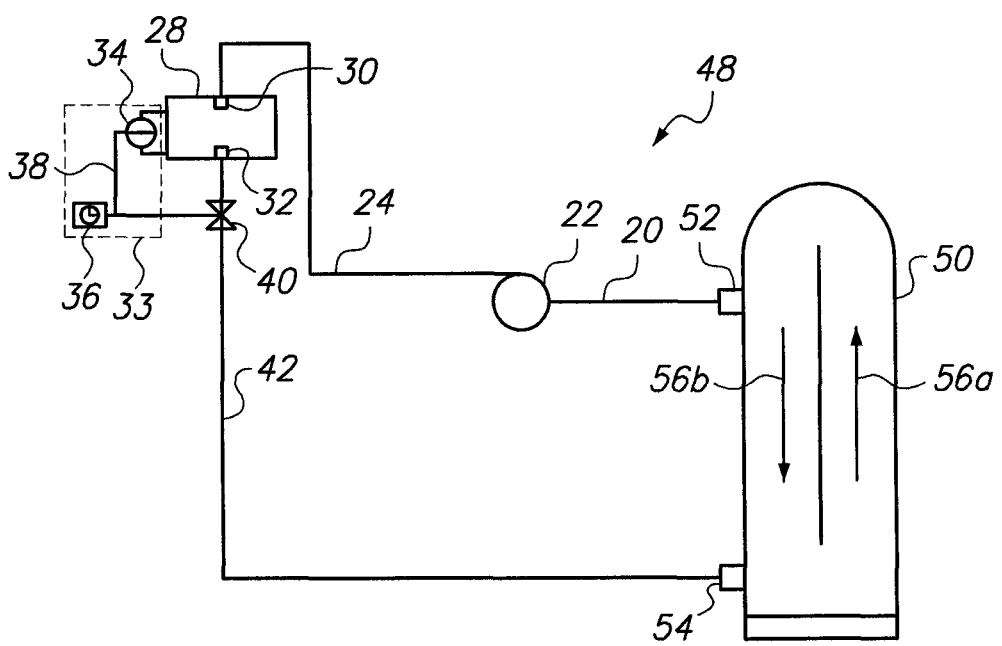
FIG. 2 is a schematic diagram of the layout of the system for the present invention when used in conjunction with a raceway pond with a circulation device.

Now referring to FIG. 2, a system 48 for the present invention, when used in conjunction with a raceway pond 50 containing algal culture, is shown. In this embodiment, many of the components are identical to the embodiment shown in FIG. 1. In the system 48, a circulation pump 22 removes an effluent of the algal culture out of the raceway pond 50 through a drainage point 52 into the transfer pipe 20. The effluent then moves through the circulation pump 22 and into the conduit 24 connected to the inlet 30 of the flush tank 28. Like the system 10 in FIG. 1, the activator 33, comprising a level switch 34 or a timer 36, controls the opening of the gate valve 40 which allows the effluent to be released from the flush tank 28 through its outlet 32. Once released, the effluent travels rapidly through transfer pipe 42 and into the raceway pond 50 through an inlet 54 to create a pulse flow. In system 48, the pulse flow will generate turbulence to force algae settled on the bottom of the raceway pond 50 off of the bottom and back into the culture which is flowing in the direction of arrows 56a-b. In addition, if the raceway pond 50 has a cover (not shown), algae attached to the cover will be dislodged and flow around the raceway pond 50.

Unlike the system 10 in FIG. 1, a gas exchange tank 44 is not required for the system 48 shown in FIG. 2 because the raceway pond 50 is an open system, unlike the photbioreactor 12 which is a closed system. Thus, carbon-based nutrients are easier to add directly to an open system like the raceway pond 50. But, a gas exchange tank 44 and associated equipment (i.e. diverting valve 26 and return pipe 46) can be added to the system 48, if desired, in a similar configuration as shown in FIG. 1. Alternatively, the gas exchange can take place in the flush tank 28.

Figure 3:
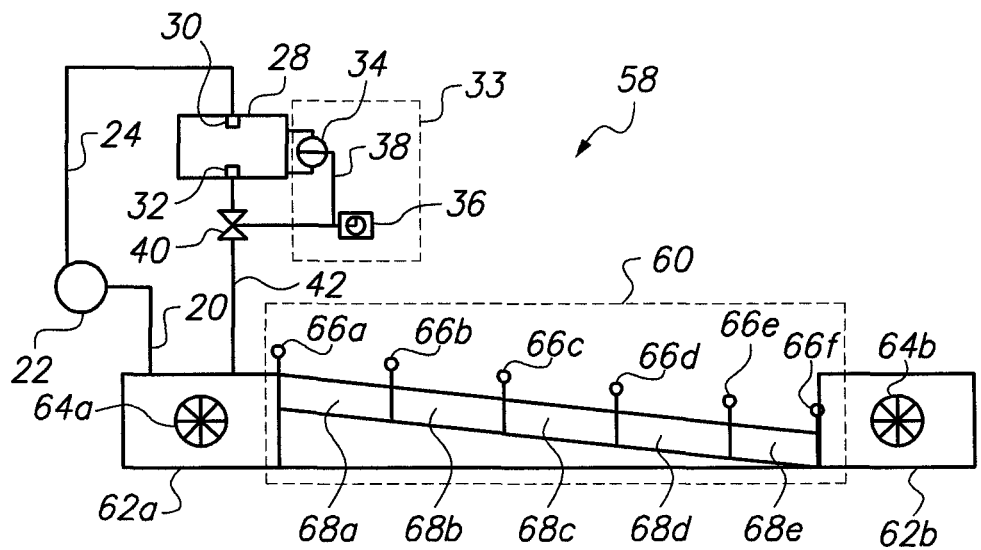
FIG. 3 is an elevation view of the system of the present invention when used in conjunction with a sloped pond without a circulation device.

Now referring to FIG. 3, a system 58 is shown when adapted for use with a sloped pond 60. As can be seen, the circulation pump 22, the flush tank 28, level switch 34, timer 36, and gate valve 40 are substantially identical and operate in the same manner as systems 10 and 48 in FIG. 1 and FIG. 2 respectively. Importantly, the pulse flow is created in the same manner with effluent being released from the flush tank 28. Instead of entering a photobioreactor 12 or a raceway pond 50, the pulse flow enters a sump 62a before reaching the sloped pond 60. When a sloped pond 60 is used for algae cultivation, a main pump 64a, housed within the sump 62a, is provided to initiate fluid flow. As shown in FIG. 3, the sloped pond 60 is constructed with a plurality of flush gates 66a-f, with the area between consecutive flush gates 66a-f being referred to as a segment 68a-e. At the end of the last segment 68e, sump 62b, housing another main pump 64b, leads to another sloped pond (not shown). It should be noted that the system 58 may also be constructed with flush gate 66a only. With only flush gate 66a, the pulse flow will travel through the entire length of the sloped pond 60 when released from the flush tank 28. When using a plurality of flush gates 66a-f, the pulse flow can be controlled as all of the flush gates 66a-f can be opened simultaneously (in the same manner as when only flush gate 66a is used), or the flush gates 66a-f can be opened one at a time. If one flush gate is opened at a time, the pulse flow will travel through one segment 68a-e at a time.

Still referring to FIG. 3, an alternate embodiment may also be described. In this alternate embodiment, the flush tank 28 is replaced by the sump 62 and houses pump 64a. In this configuration, the circulation pump 22 can be eliminated because pump 64a is configured to produce the pulse flow. With the height of the flush tank 28 eliminated, pump 64a will be constructed to compensate for the lack of gravity flow by having the ability to produce the high fluid flow rate required to produce the pulse flow. Without a flush tank 28, the level switch 34 or timer 36 are incorporated with the sump 62 and main pump 64a. In this arrangement, the main pump 64a is configured to create a pulse flow, and instead of a gate valve 40, the flush gate 66a serves to release the effluent from the sump 62. The level switch 34 or timer 36 can be set to open the flush gates 66a-f in any sequence.

Figure 4:
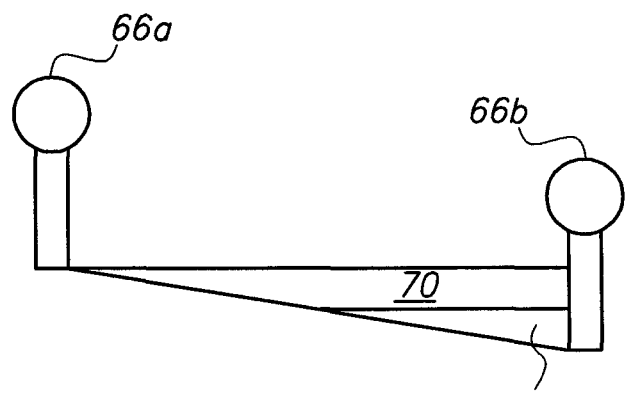
FIG. 4 is a detail of one section of the system of the present invention when used in conjunction with a sloped pond.

Referring now to FIG. 4, a detail of a segment between two flush gates 66a-b is shown. In FIG. 4, the concept of light and dark cycles is illustrated. In more detail, when flush gates 66a-b are in a closed position, a portion of effluent remains between the flush gates 66a-b. As shown, the effluent between the gates 66a-b will generally settle in two layers or zones, a light zone 70 and a dark zone 72. Algae cells in the effluent which settle in the light zone 70 will have an increased exposure to the light necessary for photosynthesis. At the same time, the algae cells which settle in the effluent in the dark zone 72 are not exposed to enough light for photosynthesis to occur. By using the pulse flow to create turbulence to stir up, or mix, the algal culture, nearly all of the algae cells will be exposed to a suitable amount of light for photosynthesis during one or more flush cycles.

While the System and Method for Using a Pulse Flow Circulation for Algae Cultivation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for using a pulse flow to circulate algae in an algae cultivation apparatus comprises:
   an algae cultivation apparatus for growing an algal culture containing a biomass;
   a flush tank positioned at an elevation above the algae cultivation apparatus for receiving an effluent of the algal culture to be used to create a pulse flow into the algae cultivation apparatus;
   a circulation pump connected to the algae cultivation apparatus, wherein the circulation pump draws the effluent of the algal culture from the algae cultivation apparatus and transfers the effluent to the flush tank via a conduit and wherein the conduit has a first end in contact with the algae cultivation apparatus and a second end connected to the circulation pump; and
   an activator, wherein the activator includes a timer set to a predetermined time interval to govern the release of the effluent from the flush tank into the conduit to create a pulse flow of effluent through the algae cultivation apparatus.

2. The system as recited in claim 1 further comprising:
   a gate valve connected between the flush tank and the algae cultivation apparatus for controlling the release of the effluent from the flush tank to the algae cultivation apparatus; and
   a transfer pipe having an inlet and an outlet, wherein the inlet is connected to the flush tank and the outlet is connected to the algae cultivation apparatus.

3. The system as recited in claim 1 wherein the algae cultivation apparatus is a photobioreactor.

4. The system as recited in claim 1 wherein the algae cultivation apparatus is a sloped cultivation pond.

5. The system as recited in claim 4 wherein the cultivation pond includes a device selected from a group comprising a paddle and a circulation pump to keep the algae in continuous motion.

6. The system as recited in claim 1 wherein the activator is a level switch, wherein the level switch is activated when the effluent in the flush tank reaches a predetermined level.

7. The system as recited in claim 4 further comprising:
   a plurality of flush gates, wherein the area between consecutive flush gates defines a flush segment; and
   a main pump for circulating algal culture through the cultivation pond.

8. The system as recited in claim 7 wherein the plurality of flush gates are opened simultaneously.

9. The system as recited in claim 7 wherein the plurality of flush gates are opened sequentially.

10. A system for using a pulse flow to circulate algae in an algae cultivation apparatus comprises:
    an algae cultivation apparatus for growing an algal culture containing a biomass;
    a flush tank positioned at an elevation above the algae cultivation apparatus for receiving an effluent of the algal culture to be used to create a pulse flow into the algae cultivation apparatus;
    a circulation pump connected to the algae cultivation apparatus, wherein the circulation pump draws the effluent of the algal culture from the algae cultivation apparatus and transfers the effluent to the flush tank via a conduit and wherein the conduit has a first end in contact with the algae cultivation apparatus and a second end connected to the circulation pump;

an activator, wherein the activator is selectively activated to release the effluent from the flush tank into the conduit to create a pulse flow of effluent through the algae cultivation apparatus;

a gas exchange tank in fluid communication with the algae cultivation apparatus for receiving a portion of the effluent from the algae cultivation apparatus, wherein the gas exchange tank enriches the effluent with $CO_2$;

a diverting valve connected between the gas exchange tank and the algae cultivation apparatus, wherein the diverting valve controls the flow of effluent from the algae cultivation apparatus to the gas exchange tank; and a return pipe connected between the gas exchange tank and the algae cultivation apparatus for returning the $CO_2$-enriched effluent back to the algae cultivation apparatus.

11. A system for using a pulse flow to circulate algae in an algae cultivation system which comprises:

a cultivation pond for cultivating an algal culture, wherein the cultivation pond is constructed with a plurality of flush gates, wherein the area between the flush gates is a flush segment;

a main pump for circulating the algal culture through the cultivation pond;

a sump, wherein the sump is used to store the algal culture, wherein the algal culture is forcibly released from the sump to create a pulse flow of algal culture through the cultivation pond, and wherein the pulse flow travels one segment at a time when the flush gates are opened in sequential order; and an activator for initiating the release of the algal culture from the sump to the cultivation pond.

12. The system as recited in claim 11 wherein the activator comprises a timer, wherein the timer is electrically connected to each flush gate to control the opening of each flush gate according to a predetermined time interval.

13. The system as recited in claim 11 wherein the activator comprises a level switch to measure the amount of algal culture in the sump, wherein the level switch can initiate the release of algal culture from the flush tank when the amount of algal culture reaches a predetermined level in the flush tank.

* * * * *